United States Patent
Cho

(10) Patent No.: US 10,251,769 B2
(45) Date of Patent: Apr. 9, 2019

(54) HEALTH FUNCTIONAL SELF-ADHESIVE INNER WEAR

(71) Applicant: ODOROSO CO., LTD., Seoul (KR)

(72) Inventor: Na-Yun Cho, Seoul (KR)

(73) Assignee: WAVE COMPANY CO., LTD. (KR)

( * ) Notice: Subject to any disclaimer, the term of this patent is extended or adjusted under 35 U.S.C. 154(b) by 358 days.

(21) Appl. No.: 15/166,755

(22) Filed: May 27, 2016

(65) Prior Publication Data
US 2016/0270947 A1  Sep. 22, 2016

Related U.S. Application Data

(63) Continuation of application No. PCT/KR2014/010308, filed on Oct. 30, 2014.

(30) Foreign Application Priority Data

May 9, 2014 (KR) .................. 10-2014-0055267

(51) Int. Cl.
*A61F 5/01* (2006.01)
*A61F 5/37* (2006.01)
(Continued)

(52) U.S. Cl.
CPC .................. *A61F 5/37* (2013.01); *A41B 1/08* (2013.01); *A61F 5/01* (2013.01); *A61F 13/023* (2013.01);
(Continued)

(58) Field of Classification Search
CPC .... A41B 9/00; A41B 9/02; A41B 9/12; A41B 17/00; A41B 11/14; A41B 9/06;
(Continued)

(56) References Cited

U.S. PATENT DOCUMENTS 8,578,514 B2  11/2013  Caillibotte et al.
2005/0054251 A1  3/2005  Kropke et al.

FOREIGN PATENT DOCUMENTS

JP  11-323636 A  11/1999
KR  10-0527561 B1  11/2005
(Continued)

OTHER PUBLICATIONS

WIPO, International Search Report (PCT/KR2014/010308), dated Jan. 30, 2015.

*Primary Examiner* — Ophelia A Hawthorne
(74) *Attorney, Agent, or Firm* — Park & Associates IP Law, P.C.

(57) ABSTRACT

Health functional self-adhesive inner wear having a kinesio tape adhered to the inner surface thereof, includes: a base layer adhered to the inner surface of the inner wear; a health functional material layer laminated on the base layer; and a self-adhesive layer laminated on the health functional material layer and making contact with the skin, wherein the base layer is adhered to the inner surface of the inner wear by applying liquid silicon to the inner surface of the inner wear in a printing manner such that the base layer is adhered to the inner wear by means of thermal curing in a state in which a portion of the liquid silicon is absorbed into the inner wear, and wherein the health functional materials contained in the health functional material layer are different depending on the application part of a human body with which the self-adhesive layer of the kinesio tape makes contact or a symptom of the corresponding body part.

3 Claims, 2 Drawing Sheets

(51) Int. Cl.
*A61F 13/02* (2006.01)
*A41B 1/08* (2006.01)
*B32B 7/12* (2006.01)
*A41B 9/12* (2006.01)

(52) U.S. Cl.
CPC ............ *A61F 13/0253* (2013.01); *B32B 7/12* (2013.01); *A41B 9/12* (2013.01); *A41B 2400/32* (2013.01); *B32B 2250/02* (2013.01); *B32B 2250/03* (2013.01); *B32B 2250/44* (2013.01); *B32B 2255/26* (2013.01); *B32B 2264/00* (2013.01); *B32B 2264/102* (2013.01); *B32B 2405/00* (2013.01); *B32B 2437/00* (2013.01); *B32B 2535/00* (2013.01); *B32B 2556/00* (2013.01)

(58) Field of Classification Search
CPC ...... A41B 1/08; A41B 2400/32; A41D 13/00; A41D 19/00; B32B 27/12; B32B 5/02; B32B 7/12; B32B 2250/02; B32B 2250/03; B32B 2250/44; B32B 2255/26; A41C 1/00; A61F 5/37; A61F 5/01; A61F 13/023; A61F 13/0253; A61F 13/02
See application file for complete search history.

(56) References Cited

FOREIGN PATENT DOCUMENTS

| | | |
|---|---|---|
| KR | 20-0415396 Y1 | 5/2006 |
| KR | 10-2007-0024177 A | 3/2007 |
| KR | 10-2009-0107989 A | 10/2009 |
| KR | 10-2013-0013433 A | 2/2013 |
| KR | 10-1268599 B1 | 5/2013 |

HEALTH FUNCTIONAL SELF-ADHESIVE INNER WEAR

REFERENCE TO RELATED APPLICATIONS

This is a continuation of pending International Patent Application PCT/KR2014/010308 filed on Oct. 30, 2014, which designates the United States and claims priority of Korean Patent Application No. 10-2014-0055267 filed on May 9, 2014, the entire contents of which are incorporated herein by reference.

FIELD OF THE INVENTION

The present invention relates to a health functional self-adhesive inner wear, and more particularly, to a health functional self-adhesive inner wear that provides health functionalities different from each other according to the parts of the human body.

BACKGROUND OF THE INVENTION

Korean Patent Registration No. 1268599, patented by this inventor discloses a functional elastic inner wear to which a kinesio tape elastically directly contacting the skin of the human body when worn, having a predetermined pattern corresponding to each part of the human body, and formed of a silicon material having self-adhesion is adhered to an inner surface thereof, wherein the kinesio tape is adhered to the skin by using the self-adhesion thereof to lift the skin according to the motion of the human body.

According to the foregoing patent, the functional elastic inner wear may have effects in assisting musculoskeletal and ligament functions for each parts of the human body, preventing secondary damage from occurring, supporting a wounded part, and providing a smooth flow of blood in the blood circulation system and a superior taping therapy effect in adhering the tape to an accurate position for each parts of the human body without being changed in position and generating a gap between the skin and the tape even though the motion of the human body occurs.

However, the foregoing patent has the following problems.

First, there is a method in which liquid silicon is applied and cured to adhere the kinesio tape to the inner wear as a method having good production efficiency among methods of adhering the kinesio tape formed of the silicon material to the inner surface of the inner wear. When the liquid silicon is actually applied to the inner surface of the inner wear, the liquid silicon may be absorbed to the inner wear. Thus, it may be difficult to form the kinesio tape having a uniform thickness.

Second, as the skin is simply lift by the kinesio tape, a space between the skin and the muscle may be generated. As a result, lymph may smoothly flow through the space, and simultaneously, blood in the blood vessels may smoothly flow while the blood vessels are expanded. However, since other health functionalities except for the foregoing functionalities are not provided, the range of use of the inner wear may be limited.

SUMMARY OF THE INVENTION

Thus, an object of the present invention is to provide a health functional self-adhesive inner wear to which a kinesio tape provided with a component that is capable of being easily adhered to an inner surface thereof is adhered.

Another object of the present invention is to provide a health functional self-adhesive inner wear, which respectively provides health functionalities different from each other to parts of the human body to expand the range of use thereof.

An object of the present invention is achieved by a health functional self-adhesive inner wear including a kinesio tape adhered to an inner surface of the inner wear, wherein the kinesio tape includes: a base layer adhered to the inner surface of the inner wear; a health functional material layer laminated on the base layer; and a self-adhesive layer laminated on the health functional material layer to contact a skin, wherein liquid silicon is applied to the inner surface of the inner wear in a printing manner and thermally cured in a state in which a portion of the liquid silicon is absorbed into the inner wear to allow the base layer to be adhered to the inner wear, and health functional materials contained in the health functional material layer are different from each other according to parts of a human body contacting the self-adhesive layer of the kinesio tape or symptoms of the corresponding parts.

Preferably, the health functional materials contained in the health functional material layer may have densities different from each other according to the parts of the human body.

Preferably, the kinesio tape may be provided in plurality and the plurality of kinesio tapes may be adhered to the inner surface of the inner wear and respectively include self-adhesive layers having thicknesses different from each other.

According to the above-described structure, the liquid silicon may be printed on the inner wear and cured to previously form the base layer contacting the inner wear. Thus, even though the liquid silicon is applied so as to form the health functional material layer or the self-adhesive layer, since the liquid silicon is not absorbed to the inner wear, the kinesio tape may be production efficiently manufactured.

Also, the musculoskeletal and ligament functions for each parts of the human body may be assisted by the specific pattern of the kinesio tape to prevent the occurrence of the secondary damage and support the wounded part. Particularly, even though the motion of the human body occurs, the state in which the kinesio tape is adhered to the corresponding part may be maintained by the self-adhesion of the kinesio tape to prevent the gap from being generated between the skin and the kinesio tape, thereby realizing the superior taping therapy effect.

Also, the smooth flow of the blood in the blood circulation system may be provided by the self-adhesion of the silicon material of the kinesio tape itself, and the health functionality may be provided in the state in which the blood and the lymph are smoothly circulated by the health functional material contained in the health functional material layer. Therefore, the effects of the kinesio tape may be more improved.

DETAILED DESCRIPTION OF THE INVENTION

Hereinafter, embodiments of the present invention will be described in detail with reference to the accompanying drawings.

Figure 1:
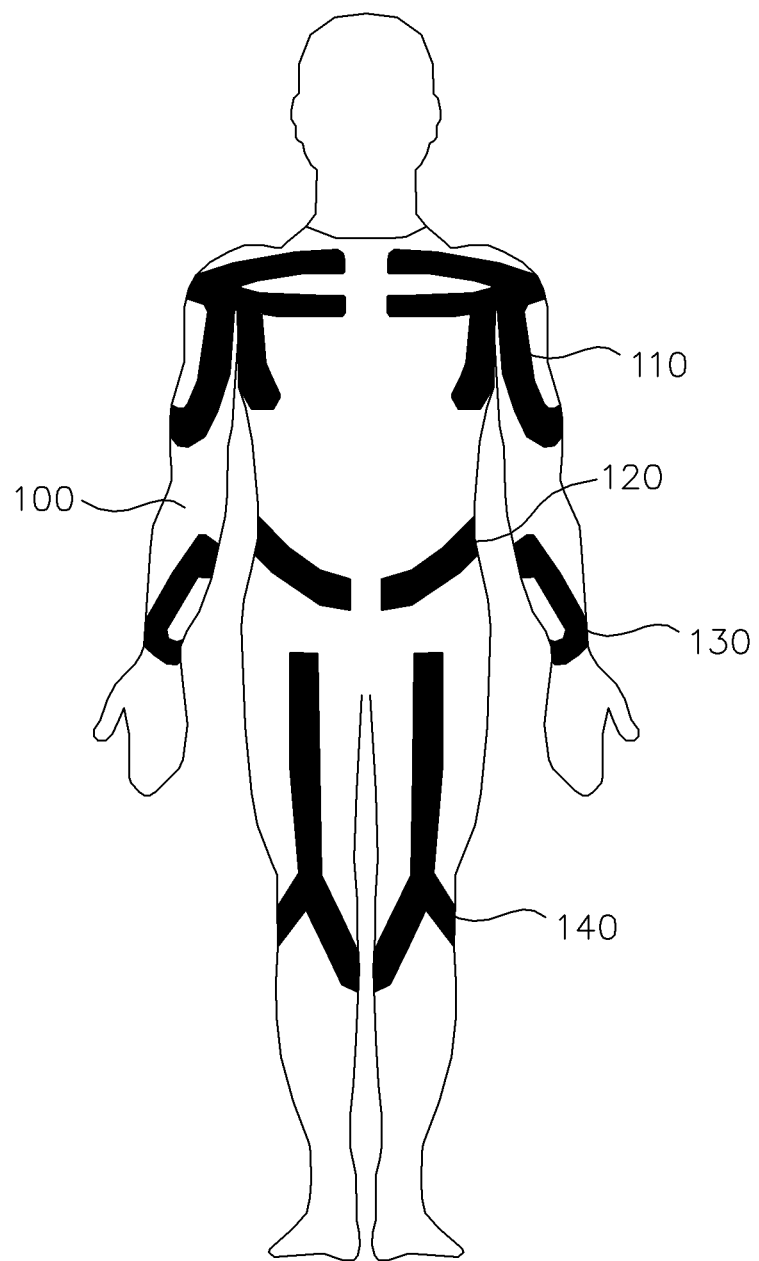
FIG. 1 is a view illustrating a state in which a health functional self-adhesive inner wear is worn according to the present invention.
Figure 2:
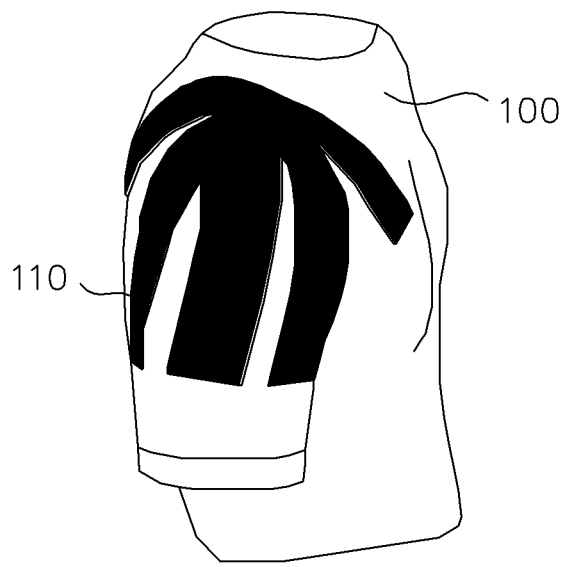
FIG. 2 is a view illustrating one example of the health functional self-adhesive inner wear.
Figure 3:
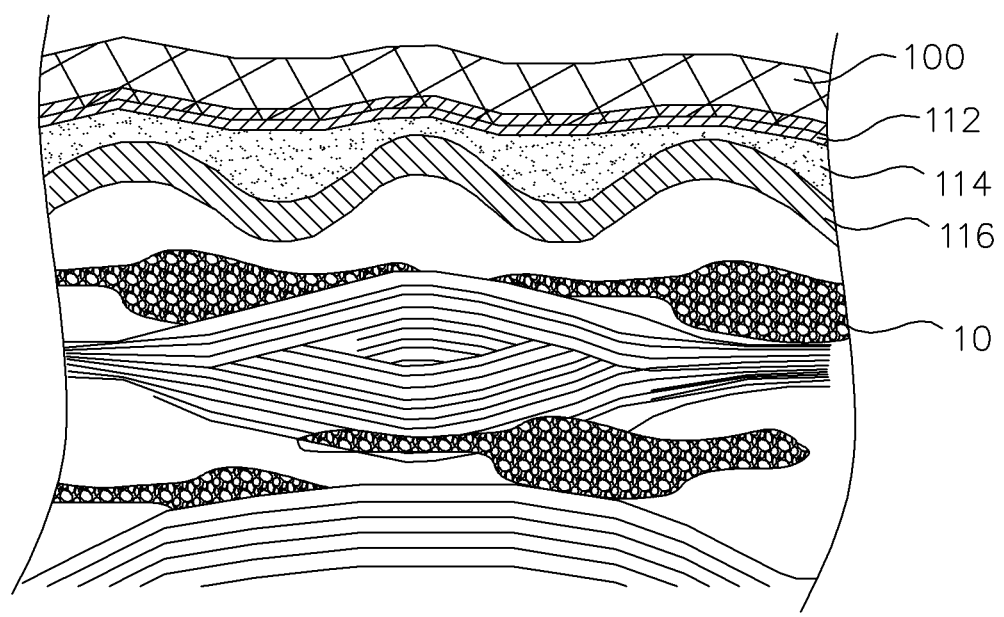
FIG. 3 is a cross-sectional view of a kinesio tape adhered to an inner surface of the health functional self-adhesive inner wear.

FIG. 1 is a view illustrating a state in which a health functional self-adhesive inner wear is worn according to the present invention, FIG. 2 is a view illustrating one example of the health functional self-adhesive inner wear, and FIG. 3 is a cross-sectional view of a kinesio tape adhered to an inner surface of the health functional self-adhesive inner wear.

A health functional self-adhesive inner wear 100 according to the present invention literally means an inner wear to which kinesio tapes that has health functionalities and directly contacts and is adhered to a skin of the human body by self-adhesion thereof are adhered.

Kinesio tapes 110, 120, 130, and 140 may be adhered to an inner surface of the inner wear 100 in a predetermined pattern according to parts of the human body or symptoms of the corresponding parts. For example, as illustrated in FIG. 1, the kinesio tapes 110, 120, 130, and 140 may be adhered to the inner surface of the inner wear 100 at positions corresponding to a shoulder, an arm and wrist, a knee, and a side and stomach of the human body. Here, the kinesio tapes 110, 120, 130, and 140 may have patterns different from each other. For example, as illustrated in FIG. 2, the inner wear 100 may be provided in the form of a T-shirt to which the kinesio tape 110 is adhered to only the part corresponding to the shoulder.

Referring to FIG. 3, the kinesio tape 110 includes a base layer 112 is directly adhered to the inner surface of the inner wear 100, a health functional material layer 114 laminated on the base layer 122, and a self-adhesive layer 116 laminated on the health functional material layer 114 to contact a skin 10.

The health functional material layer 114 may contain health functional materials different from each other according to symptoms of parts of the human body, which contact the self-adhesive layer 116.

As described above, the plurality of kinesio tapes 110, 120, 130, and 140 may be adhered to the inner surface of one inner wear 100. Each of the health functional material layers 114 of the kinesio tapes 110, 120, 130, and 140 may contain health functional materials, which respectively have components different from each other.

Also, the health function material of each of the health functional material layers 114 may be adjusted in density to adjust intensity of the health functionality.

Since the self-adhesive layer 116 is formed by curing the liquid silicon, the self-adhesive layer 116 has elasticity and self-adhesion. The skin 10 of the human body to which the kinesio tape 110 is applied may elastically receive a pressure from the inner wear 100 by the elasticity of the self-adhesive layer 116. When a person wears the inner wear 100 and moves, the skin 10 may be always lifted by the self-adhesion of the kinesio tape 100 adhered to the inner wear 110.

Each of the base layer 112 and the self-adhesive layer 116 is formed of a silicon material. However, since the base layer 112 is firmly adhered to the inner wear 100 and the self-adhesive layer 116 is self-adhered to the skin 10, the base layer 112 and the self-adhesive layer 116 may have compositions different from each other in consideration of a curing speed and the self-adhesion of the silicon material.

Also, it is unnecessary to match a shape of the self-adhesive layer 116 contacting the skin 10 and a shape of the health functional material layer 114 with each other. However, it is preferred that the self-adhesive layer 116 and the health functional material layer 114 have the same shape because blood and lymph are smoothly circulated when the skin 10 is lifted by the self-adhesive layer 116, and, in this state, the health functionality due to the health functional material layer 114 is efficiently provided.

The self-adhesive layer 116 may be controlled in thickness to adjust the elasticity and the pressure force. For example, since the inner wear 100 has a predetermined size, when the self-adhesive layer 116 has a thicker thickness at a specific part of the human body, force for pressing the skin 10 by the self-adhesive layer 116 at the specific part may increase.

Hereinafter, an example of a method for forming each constituent will be described.

In case of the base layer 112, when the liquid silicon is applied to the inner surface of the inner wear 100 in a printing manner, a portion of the applied liquid silicon is absorbed to the inner wear 100. In this state, the liquid silicon is quickly thermally cured to form the base layer 112. Thus, base layer 112 may be firmly adhered by the curing of the liquid silicon absorbed to the inner wear 100.

It is preferred that the base layer 112 is formed in a pattern corresponding to the preset pattern of the self-adhesive layer 116. However, the present invention is not limited thereto.

A liquid mixture in which powder of a material having the health functionality is uniformly dispersed into and mixed with the liquid silicon may be applied onto the cured base layer 112 and then cured to form the health functional material layer 114.

Various health functional materials may be provided. Thus, corresponding health functional materials may be used according to parts of the human body or symptoms of the parts of the human body, respectively.

For example, platinum powder may be applied to a person having a relatively high body temperature, and gold powder may be applied to a person that frequently emits cold sweat or gives too much smell of sweat. Here, the kinesio tape 110 including platinum power or gold power may be adhered to the persons in a pattern that passes through an armpit or groin.

Also, the kinesio tape 110 including sodalite may be adhered to a person having liver or kidney failure in a pattern that passes through the liver and the kidney.

In addition to the above-described example, various kinds of health functional materials may be applied. For example, far infrared ray generating materials such as tourmaline or kaolin, anion-generating materials, germanium, bioceramic powder, oriental medicine extracts, and the like may be applied.

The liquid silicon may be applied to the cured health functional material layer 114 and then cured to form the self-adhesive layer 116.

When the inner wear 100 to which the kinesio tape 110 is attached to the inner surface thereof is worn, the self-adhesive layer 116 of the kinesio tape 110 is adhered to the skin 10 to lift the skin 10 according to the movement of the muscle, thereby allowing the blood and the lymph to be smoothly circulated.

Also, as described above, the health functional materials contained in the health functional material layer 114 may provide health functionalities different from each other according to the parts of the human body. Here, since the health functionalities due to the health functional materials are provided in the state in which the blood and the lymph are smoothly circulated, their effects may be more improved.

For example, when platinum powder or gold powder is used as the health functional material, kinesio tape 110 is adhered to a redolent armpit or groin, the health functional material may reduce an occurrence of sweat and reduce smell of sweat.

When the kinesio tape 110 is adhered to a position of the human body, at which the bone-skeleton and the ligament coexist, e.g., the shoulder, and the like, the movement of the shoulder joint may be restricted by elastic restoring force of the kinesio tape 110 to assist the functions of the bone-skeleton and the ligament of the shoulder part, prevent the secondary damage, and support the wounded part. Particularly, since the kinesio tape 110 is adhered to contact the skin 10 to provide the self-adhesion and the kinesio tape 111 itself has the elasticity, the kinesio tape 110 adhered to the skin 10 is minimized in movement in spite of the motion of the user and thus adhered to and maintained at the accurate part of the human body.

As described above, the liquid silicon may be printed on the inner wear and cured to previously form the base layer contacting the inner wear. Thus, even though the liquid silicon is further applied so as to form the health functional material layer or the self-adhesive layer, since the liquid silicon further applied is not absorbed to the inner wear, the kinesio tape may be efficiently manufactured.

Also, the kinesio tape itself may have following advantages.

That is, the musculoskeletal and ligament functions for each parts of the human body may be assisted by the specific pattern of the kinesio tape to prevent the occurrence of the secondary damage and support the wounded part. Particularly, even though the motion of the human body occurs, the state in which the kinesio tape is adhered to the corresponding part may be maintained by the self-adhesion of the kinesio tape to prevent the gap from being generated between the skin and the kinesio tape, thereby realizing the superior taping therapy effect.

Also, the smooth flow of the blood in the blood circulation system may be provided by the self-adhesion of the silicon material of the kinesio tape itself, and the health functionality may be provided in the state in which the blood and the lymph are smoothly circulated by the health functional material contained in the health functional material layer. Therefore, the effects of the kinesio tape may be more improved.

Although the exemplary embodiment of the present invention has been shown and described above, various changes and modifications which can be understood by a person skilled in the art may also be made.

For example, although the health functional material layer 114 is separately formed on the base layer 112 in the foregoing embodiment, the health functional material layer 114 may be integrally formed on the base layer 112.

Thus, the present invention should not be construed as being limited to only the foregoing embodiment, but be construed by the appended claims.

What is claimed is:

1. A health functional self-adhesive inner wear comprising:
    a kinesio tape adhered to an inner surface of the inner wear,
    wherein the kinesio tape comprises:
    a base layer adhered to the inner surface of the inner wear;
    a health functional material layer laminated on the base layer; and
    a self-adhesive layer laminated on the health functional material layer and adapted to contact a skin,
    wherein the base layer is adhered to the inner surface of the inner wear by applying liquid silicon to the inner surface of the inner wear in a printing manner and thermally cured in a state in which a portion of the liquid silicon is absorbed into the inner wear to allow the base layer to be adhered to the inner wear, and
    wherein health functional materials contained in the health functional material layer are different from each other depending on its application parts of a human body with which the self-adhesive layer of the kinesio tape is adapted to make contact or symptoms of the corresponding body parts to apply.

2. The health functional self-adhesive inner wear of claim 1, wherein the health functional materials contained in the health functional material layer have densities different from each other depending on the parts of the human body to apply.

3. The health functional self-adhesive inner wear of claim 1, wherein the kinesio tape is provided in plurality, and the plurality of kinesio tapes are adhered to the inner surface of the inner wear and respectively comprise self-adhesive layers having thicknesses different from each other.

* * * * *